(12) United States Patent
Laborde et al.

(10) Patent No.: US 10,444,142 B2
(45) Date of Patent: Oct. 15, 2019

(54) SPECTROSCOPIC DEVICE AND METHOD FOR SAMPLE CHARACTERIZATION

(71) Applicant: GREENTROPISM, Paris la Defense (FR)

(72) Inventors: Antoine Laborde, Arcueil (FR); Aude Bourdeau, Castanet Tolosan (FR); Anthony Boulanger, Paris (FR)

(73) Assignee: GREENTROPISM, Paris la Defense (FR)

( * ) Notice: Subject to any disclaimer, the term of this patent is extended or adjusted under 35 U.S.C. 154(b) by 0 days.

(21) Appl. No.: 15/946,887

(22) Filed: Apr. 6, 2018

(65) Prior Publication Data

US 2018/0299373 A1    Oct. 18, 2018

(30) Foreign Application Priority Data

Apr. 7, 2017   (EP) .................................... 17305412

(51) Int. Cl.
*G01N 21/31*    (2006.01)
*G01J 3/28*     (2006.01)
(Continued)

(52) U.S. Cl.
CPC .......... *G01N 21/314* (2013.01); *G01J 3/0264* (2013.01); *G01J 3/28* (2013.01);
(Continued)

(58) Field of Classification Search
CPC .... G01N 21/314; G01N 21/274; G01N 21/31; G01N 33/10; G01N 2201/121;
(Continued)

(56) References Cited

U.S. PATENT DOCUMENTS 5,614,718 A * 3/1997 Brace ................. G01N 21/3504
                                                  250/339.07
6,122,052 A * 9/2000 Barnes ..................... G01J 3/28
                                                       356/328
(Continued)

FOREIGN PATENT DOCUMENTS

CN        106124451 A     11/2016

OTHER PUBLICATIONS

European Search Report for 17305412.3 dated Nov. 6, 2017.
(Continued)

*Primary Examiner* — Dominic J Bologna
(74) *Attorney, Agent, or Firm* — Meagher Emanuel Laks Goldberg & Liao, LLP

(57) ABSTRACT

The invention relates to a characterization device (50) for characterizing a sample (S) comprising:
  a memory (MEM) storing a measured spectrum ($A_{s+p}$) of said sample, performed through a translucent material, and a measured spectrum of the translucent material ($A_p$),
  a processing unit (PU) configured to:
    determine a spectral energy ($E_{s+p}$) of the measured spectrum ($A_{s+p}$) of the sample through the translucent material ($A_{s+p}$),
    estimate a coefficient ($\hat{\gamma}$) from said spectral energy ($E_{s+p}$) and,
    determine a corrected spectrum ($\hat{A}_s$) of the sample from the measured spectrum ($A_{s+p}$) of the sample through the translucent material and from a corrected spectrum of the translucent material ($\hat{A}_p$),
said corrected spectrum of the translucent material ($\hat{A}_p$) being determined from the measured spectrum of the translucent material ($A_p$) and from the estimated coefficient ($\hat{\gamma}$).

15 Claims, 17 Drawing Sheets

(51) Int. Cl.
*G01J 3/42* (2006.01)
*G01N 33/10* (2006.01)
*G01N 21/27* (2006.01)
*G01J 3/02* (2006.01)

(52) U.S. Cl.
CPC .............. *G01J 3/42* (2013.01); *G01N 21/274* (2013.01); *G01N 21/31* (2013.01); *G01N 33/10* (2013.01); *G01J 2003/2833* (2013.01); *G01J 2003/2843* (2013.01); *G01J 2003/2866* (2013.01); *G01J 2003/2869* (2013.01); *G01J 2003/2873* (2013.01); *G01N 2201/121* (2013.01); *G01N 2201/129* (2013.01); *G01N 2201/1293* (2013.01)

(58) Field of Classification Search
CPC ...... G01N 2201/129; G01N 2201/1293; G01J 3/0264; G01J 3/28; G01J 3/42; G01J 2003/2833; G01J 2003/2843; G01J 2003/2866; G01J 2003/2869; G01J 2003/2873
See application file for complete search history.

(56) References Cited

U.S. PATENT DOCUMENTS

| | | | | |
|---|---|---|---|---|
| 2009/0321646 | A1* | 12/2009 | Cozzolino | G01N 21/31 250/339.05 |
| 2012/0014572 | A1* | 1/2012 | Wong | G01J 3/46 382/128 |
| 2013/0297254 | A1* | 11/2013 | Vignesh | G01N 21/65 702/179 |

OTHER PUBLICATIONS

R. Beghi et al.: "Influence of packaging in the analysis of fresh cut *Valerianella locusta* L. and golden delicious apple slices by visible-near IR and near-IR spectroscopy", Journal of Food Engineering, vol. 171, Feb. 2016 (Feb. 2016), pp. 145-152.

* cited by examiner

FIG.8bis

SPECTROSCOPIC DEVICE AND METHOD FOR SAMPLE CHARACTERIZATION

BACKGROUND

Field

The invention relates in general to the field of characterization of a sample by spectrometry. In particular the invention relates to a device and a method to determine a corrected spectrum of a sample from an initial measured spectrum of the sample performed through a translucent material such as a transparent packaging. The corrected spectrum is then able to be introduced into a characterization model to perform classification or quantification operations on the sample.

Related Art

In the frame of spectroscopy, and more particularly infrared (IR) spectroscopy, the optical properties of a sample are determined by measuring the intensity I0 incident on the sample S, and the intensity I transmitted or reflected by the sample, for a plurality of wavelengths inside a specific range [$\lambda 1; \lambda 2$], as shown on FIG. 1 in the case of a reflective sample S. The interaction between the light and the sample permits the characterization of the sample.

The different wavelengths are generated by a light source LS, and the reflected (or transmitted) intensity is measured on a detector D. A processing unit PU calculates the spectrum $Ss(\lambda)$ corresponding to a signal, dependant on $\lambda$, determined from the ratio between I and I0 or its inverse.

The term spectrum describes different types of signals, for example:

In transmission the transmittance of the sample is defined as: $T(\lambda) = It(\lambda)/I0(\lambda)$ where It is the transmitted intensity In reflection the reflectance of the sample is defined as $R(\lambda) = I_R(\lambda)/I0(\lambda)$, where $I_R$ is the reflected intensity The reflection opacity $O_R(\lambda)$ is defined as $1/R$, and the transmission opacity $O_t(\lambda)$ is defined as $1/T$.

The absorbance $As(\lambda)$ is defined as:

For reflection: $As_{/R}(\lambda) = \log_{10}[I0(\lambda)/I_R(\lambda)]$

For transmission: $As_{/t}(\lambda) = \log_{10}[I0(\lambda)/I_t(\lambda)]$ (1)

The physical quantities defined as:

For reflection: $As_{/R}'(\lambda) = \log_{10}[I_R(\lambda)/I0(\lambda)]$

For transmission: $As_{/t}'(\lambda) = \log_{10}[I_t(\lambda)/I0(\lambda)]$ (2)

can also be used as a spectrum.

The absorbance $\log_{10}[I0(\lambda)/I(\lambda)]$ or $\log_{10}[I(\lambda)/I0(\lambda)]$ are used in spectroscopy, both in transmissive ($I(\lambda)=It(\lambda)$) or reflective ($I(\lambda)=I_R(\lambda)$) configurations with the benefit that multiplicative relationships are transformed into additive or subtractive relationships.

The measured spectrum $Ss(\lambda)$ is then used as an input into a characterization model CM in order for example to classify the sample or to quantify a particular compound of the sample.

An example of classification is the determination of the category of a flour sample among a plurality of predetermined categories of flours. Examples of quantification are: humidity level in a flour, quantification of gluten in a flour, percentage of cotton in a fabric . . . . Another possibility is to perform a classification of the sample by determining if a compound present in the sample is below or above a threshold. All these types of characterization models are commonly defined as classification/quantification models.

The characterization models, well known in the art, are based on a reference database DB of a substantial number of measured spectra of reference samples, of the different categories (classification) or having a different percentage of the compound to quantify (quantification).

The reference spectra of the database are used to calibrate the model, based for example on well known model such as partial least square discrimination (PLS-DA), Support Vector Machine (SVM), Linear Discriminant Analysis (LDA) or k Nearest Neighbours (kNN).

The models are trained using both reference spectra of the database and associated information related to the known class of the sample. For each type of model, different criteria are optimized in order to estimate the statistical properties of each class.

Once calibrated, the developed model CM is capable of extracting searched information such as class, quantified parameter . . . on the basis of an unknown spectrum, used as input, as illustrated on FIG. 2.

Some preprocessing can be applied to the raw spectrum before being injected into the model, such as moving average smoothing, to improve the signal to noise ratio in order to reduce the effect caused by the variability of samples.

A limitation is that the characterization model is only able to determine the searched information from a spectrum of a sample which is similar to the reference spectra of the database, that is to say that the measurement of the spectrum of the sample may be performed in a manner as close as possible to that used to measure the reference spectra of the reference samples.

In some practical cases it is necessary to perform the measurement through a transparent or translucent material, such as a packaging or a window. This may be the case for example for food, fabrics, or any kind of industrial product once packaged. Such packaging typically comprises plastic materials, such as polyethylene (PE), polypropylene (PP), polyethylene terephtalate (PET).

In view of the chemical nature of these materials, their impact on the light illuminating the sample is not negligible, due to absorption, reflection and diffusion.

FIG. 3 illustrates the influence of a PP packaging on the absorbance of a coconut flour (reflective type sample) in the IR spectrum. FIG. 3a shows the measured absorbance of the flour alone $A_s(\lambda)$, FIG. 3b shows the measured absorbance of the flour through the packaging $A_{s+p}(\lambda)$, and FIG. 3c the measured absorbance of the packaging alone $A_p(\lambda)$. The packaging alone has been measured the same way as the flour, by replacing the flour by a material having a uniform reflectivity across the IR spectrum. Each spectrum comprises an average of 30 measurements.

The measurements of $A_s$, $A_p$ and $A_{s+p}$ have been performed with the same protocol in the same conditions. It can be seen that the measured spectrum is modified by the packaging.

For example the inventors have developed a model of classification of eight types of flours. 15 measurements of each type of flour have been performed with the flour alone that is to say in the absence of packaging material, to generate the database for the classification model (120 measurements). Based on the measurements of the database, a classification model was built, capable of identifying any sample flour of one the eight types from the measured absorbance of the sample flour alone. In this particular case, the classification model was developed using a kNN type model.

Then the measured spectrum of the sample flour through four different kinds of packaging is submitted to the model.

Two physically different packaging types, composed of polyethylene (PE), are respectively named PE1 and PE2

Two physically different packaging types, composed pf polyethylene terephtalate (PET), are respectively named PET1 and PET2.

The error rate of the model becomes:

PE1: 75%
PE2: 61%
PET1: 73%
PET2: 78%

The modification of the spectrum induced by the packaging leads to a highly increased error rate when the spectrum is applied to the classification model.

The publication "Influence of packaging in the analysis of fresh cut *Valerianella locusta* L. and golden delicious apple slices by visible-near IR and near-IR spectroscopy", R. Beghi et al, Journal of Food Engineering 171 (2016), studies the influence of plastic packaging in the analysis of the freshness of apples and leaves. The paper evaluates the effect in terms of model performance. The authors explain that the packaging has a more important effect in the near IR than in the visible range, partly because of an increased absorption in this wavelength range.

A first classification model is built from a database of spectra of apples without packaging, and a second model is built from a database of spectra of apples with packaging. The performances of the two models are compared, but this publication does not try to explain nor suppress the packaging effect.

It is thus needed for an improved device and method for a robust characterization of a sample (classification/quantification) when the optical measurement leading to the characterization is performed through a translucent material disturbing the optical measurement.

SUMMARY OF THE INVENTION

In accordance with a first aspect there is provided a characterization device for characterizing a sample, said device comprising:
    a memory storing a measured spectrum of said sample, performed through a translucent material, and a measured spectrum of the translucent material,
    a processing unit configured to:
        determine a spectral energy of the measured spectrum of the sample through the translucent material,
        estimate a coefficient ($\gamma$) from said spectral energy and,
        determine a corrected spectrum of the sample from the measured spectrum of the sample through the translucent material and from a corrected spectrum of the translucent material,
        said corrected spectrum of the translucent material being determined from the measured spectrum of the translucent material and from the estimated coefficient.

According to a development of the first aspect the characterization device further comprises a modelling unit configured to implement a characterization model developed from a reference database of spectra of reference samples, said characterisation model using the corrected spectrum of the sample as input, and delivering a classification of the sample or a classification or a quantification of a compound present in the sample.

According to a further development of the first aspect the characterization device further comprises a data structuring module configured for structuring the corrected sample spectrum based on a principal component analysis, said data structuring module generating a structured corrected sample spectrum, thereby reducing the number of wavelengths of the measurement into a reduced number of variables, said structured corrected sample spectrum being the input of an improved characterization model developed from the reference database, said improved characterization model delivering a classification of the sample or a classification or a quantification of a compound present in the sample in place of said classification model.

In accordance with a second aspect there is provided a spectrophotometer comprising:
    a measuring device comprising a light source configured to illuminate a sample to characterize, said sample being illuminated through a translucent material (P), a detector configured to detect the light reflected from or transmitted by the sample, and a calculation module configured to generate a measured spectrum of said sample, and
    a characterization device.

In accordance with a third aspect there is provided a method for determining a corrected spectrum of a sample to characterize, comprising the steps of:
    loading a measured spectrum of the sample performed through a translucent material,
    loading a measured spectrum of the translucent material,
    determining a spectral energy of the measured spectrum of the sample through the translucent material,
    estimating a coefficient from said spectral energy,
    determining said corrected spectrum of the sample from the measured spectrum of the sample and from a corrected spectrum of the translucent material, said corrected spectrum of the translucent material being determined from the measured spectrum of the translucent material and from the estimated coefficient.

According to a development of the third aspect said measured spectra are expressed as absorbance.

According to a further development of the third aspect the corrected spectrum of the translucent material is determined from a product of the estimated coefficient and the measured spectrum of the translucent material.

According to a further development of the third aspect the corrected spectrum of the sample is determined by subtracting the corrected spectrum of the translucent material from the measured spectrum of the sample through the translucent material.

According to a further development of the third aspect the estimated coefficient is determined by a predetermined relationship between the spectral energy of the measured spectrum of the sample through the translucent material and the estimated coefficient.

According to a further development of the third aspect the predetermined relationship is a linear function.

According to a further development of the third aspect the method comprises a previous step of measuring the measured spectrum of the sample through the translucent material.

According to a further development of the third aspect the method comprises a step of implementing a characterization model corresponding to a classification model or a quantification model, and using the corrected spectrum as input.

According to a further development of the third aspect the method comprises a step of structuring the corrected sample spectrum based on a principal component analysis to generate a structured corrected sample spectrum, thereby reducing the number of wavelengths of the measurement into a reduced number of variables.

In accordance with a fourth aspect there is provided a method of characterization of a sample comprising a method for determining a corrected spectrum of said sample and further comprising a step of implementing an improved characterization model using the structured corrected sample spectrum as input.

BRIEF DESCRIPTION OF THE DRAWINGS

Embodiments of the present invention, and further objectives of advantages thereof, are described in details below with reference to the attached figures, wherein:

FIG. 3a is the measured absorbance of a flour alone, FIG. 3b is the measured absorbance of the flour performed through a plastic packaging and FIG. 3c is the measured absorbance of the packaging alone.

FIG. 4a illustrates the measurement with a reflective sample, FIG. 4b the measurement with a transmissive sample, the translucent material being crossed twice, FIG. 4c the measurement with a transmissive sample, the translucent material being crossed once.

FIG. 8b is illustrates a first option using PCA on the measured spectrum obtained in step 100 of the method of FIG. 5 to generate a structured spectrum.

DETAILED DESCRIPTION OF THE INVENTION

Figure 4A:
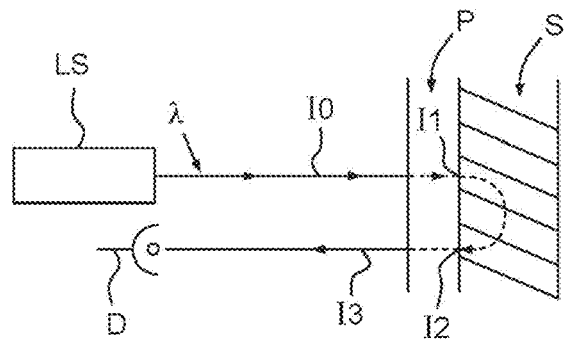
FIGS. 4a-4c illustrate the measurement of a spectrum of a sample through a translucent material by showing the path of the light from the light source to the detector.
Figure 4B:
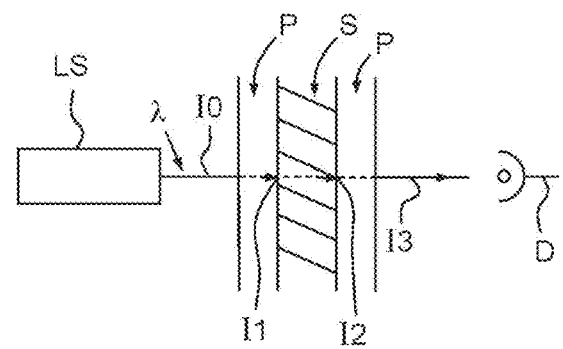
Figure 4C:
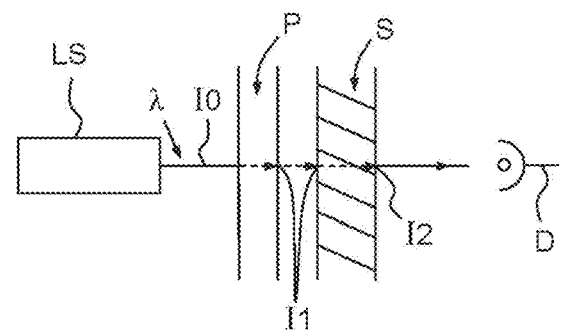

FIG. 4 shows the path of the light in a spectral measurement of a sample S through a translucent material P, which may be a plastic packaging or a window, and the corresponding intensities: FIG. 4a for the reflective case, FIG. 4b for the transmissive case, in the case where the light passes twice through the material, and 4c for the transmissive case, in the case where the light passes once through the material.

The light first passes through the material P, then through the sample S, then through the material P again (for reflective or transmissive of FIG. 4b) before reaching the detector D. In transmission, it is also possible for the light to only pass once through P.

Here the optical measurement is performed through a translucent material distorting the optical measurement, that is to say, that a transparent material is placed in the light path between the light source and the detector, in addition of the sample. The translucent material may be placed in contact with the sample. This is the case for plastic packaging of dishes. Air may be present between the translucent material and the sample, which is the case when the sample has an enclosure and is measurement through a window.

In any case the translucent material is a solid material.

For the optical measurement it is needed for a translucent material to permit the light to go through the material, and the material may also be transparent.

The measurement can be performed on a reflective sample by reflection or a transparent or translucent sample by transmission.

Throughout this document, in a non limitative way and for the purpose of clarity, the absorbance $A(\lambda)$ is used as the signal for the spectrum $S(\lambda)$, but other definitions (such as transmittance, reflectance or opacity) of the spectrum could have been used.

We define:

$A_s(\lambda)$: measured absorbance of the sample alone, $A_{s+p}(\lambda)$: measured absorbance of the sample through the translucent material P, $A_p(\lambda)$ as the measured absorbance of the translucent material alone.

The absorbance $A_p$ may be defined as the absorbance corresponding to a one way passage of the light through it or a two way, "there and back" passage.

For the case of FIGS. 4a and 4b:

$$A_{s+p} = \log_{10}[I0/I3]]$$

$$A_p = \log_{10}[I0/I1]] = \log_{10}[I2/I3]] \text{ (with Ap for a one way passage)}$$

$$A_s = \log_{10}[I1/I2]]$$

$$I0/I3 = I0/I1 * I1/I2 * I2/I3$$

This multiplicative relationship becomes an additive relationship with absorbance:

For Ap corresponding to one passage of the beam through the translucent material it can be written:

$$A_{s+p} = A_s + 2A_p$$

Or

For Ap corresponding to a there and back of the beam through the translucent material it can be written:

$$A_{s+p} = A_s + A_p \quad (3)$$

Throughout this document we will consider $A_p$ as the absorbance corresponding to the contribution of the translucent material for the measurement (there and back or one way, depending of the configuration of the measurement).

The light is affected by absorption by the molecular vibrations of the sample/material P molecules, and in a first approximation each wavelength is assumed to be independent of the others.

By using the mathematical model of formula (3), it can be deduced that for obtaining $A_s$ from $A_{s+p}$ it is sufficient to subtract $A_P$ from $A_{s+p}$.

Thus it is first needed to get the signature of each type of translucent material, meaning without the presence of any sample. A key parameter being the chemical nature of the material, it is needed to obtain the measured spectra $A_p(\lambda)$ of a set of candidate chemical types of translucent materials (PP, PET, PE . . . ).

The aim is to determine an estimated measured spectrum of the sample alone (meaning without the presence of a translucent material) named $\hat{A}_s(\lambda)$, from the measurements of $A_{s+p}$ and $A_P$, as close as possible to the "real" measured spectrum $A_s$ of the sample alone.

Applying formula (3) the estimated spectrum is:

$$\hat{A}_s = A_{s+p} - A_p \quad (4)$$

To apply this model it may be useful that the measurements of $A_p$ and $A_{s+p}$ be performed with protocol and conditions as close as possible from one measurement to the next.

This simplified model does not give satisfactory results because it appears that some spectral patterns that are reconstructed using formula (2) do not have a physical meaning. For instance, notches appear with this technique. A characterization device and method permitting a very low error rate for spectra introduced into a classification/quantification model is thus needed, where the spectra are obtained from measurements through a translucent material P such as a packaging or a window.

A tool to evaluate the performance of an estimator $\hat{A}_s$ is provided to calculate an indicator such as the root mean square error or RMSE. To perform the calculation, the "real" absorbance $A_s$ corresponding to the sample alone is needed, performed with the same protocol as the $A_p$ and $A_{s+p}$ measurements. The RMSE is:

$$RMSE = \sqrt{\frac{1}{m}\sum_{i=1}^{m}\left[\hat{A}_s(\lambda_i) - A_s(\lambda_i)\right]^2} \quad (5)$$

Where $\lambda i$, is the ith wavelength indexed from 1 to m, corresponding to the wavelengths used during the measurement.

The absolute value of the RMSE obtained for a determined estimator $\hat{A}_s$ is an imperfect indicator of the estimator quality, however the RMSE is useful to compare different estimators with one other.

Figure 5:
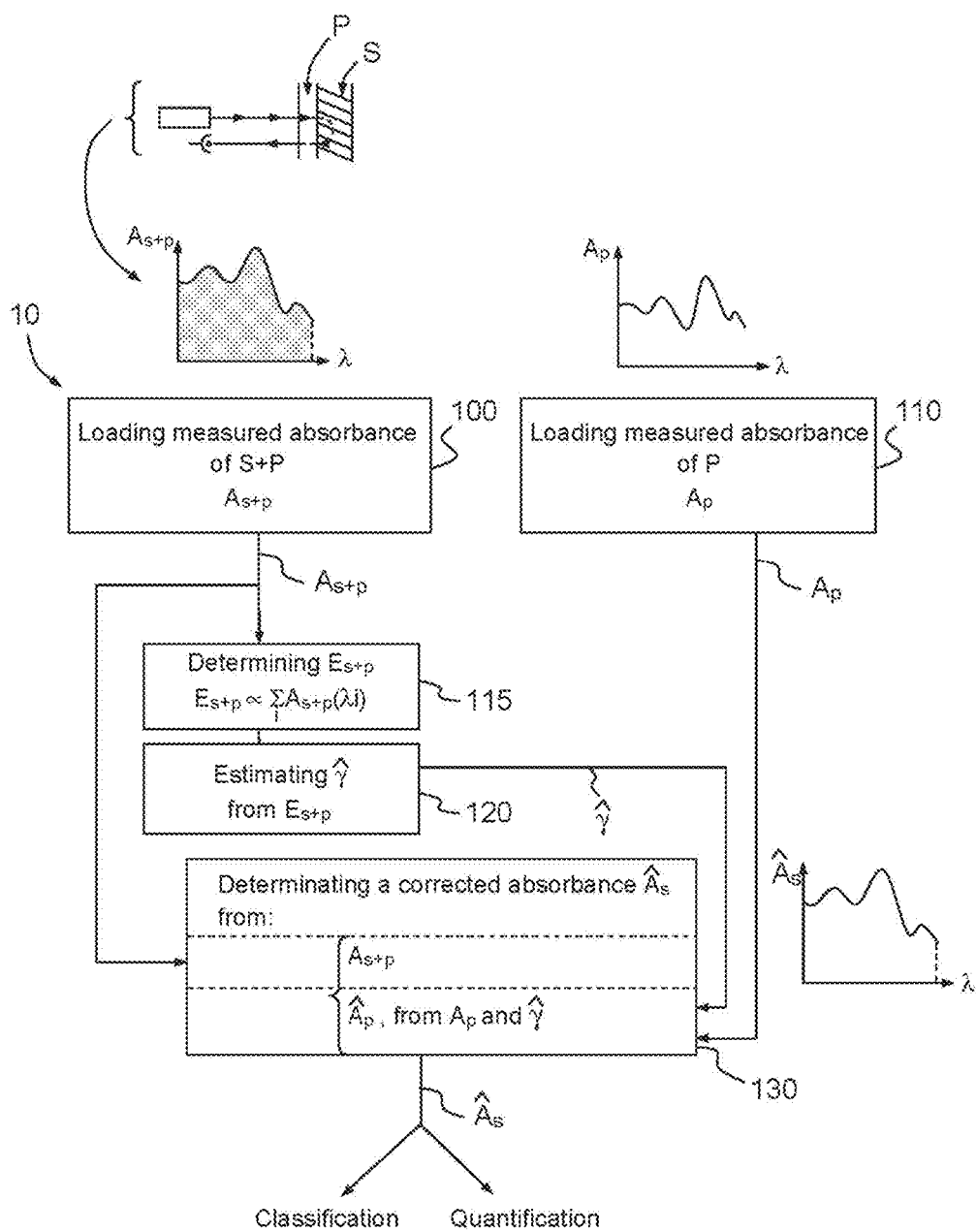
FIG. 5 illustrates the method for determining a corrected spectrum of a sample to characterize according to the invention.

FIG. 5 illustrates the method 100 for determining a corrected spectrum $\hat{A}_s$ of a sample S to characterize according to the invention.

In a first step 100, a measured spectrum $A_{s+p}$ of the sample performed through a translucent material P is loaded.

The translucent material has a chemical type, a certain thickness, and may present different physical aspects.

The measure of the spectrum was performed by an optical measurement, the optical measurement being distorted by the presence of a translucent material positioned on the light path. The spectrum is defined as a signal, dependant on the wavelength, arriving on the detector after passing through the translucent material and the sample.

In a second step 110 a measured spectrum of the translucent material alone $A_p$ is loaded.

This spectrum Ap may be obtained by a measurement made in a comparable or equivalent way as the sample spectrum or may be available from a database DBP insofar as its chemical type is known. The two measured spectra $A_{s+p}$ and $A_p$ may be performed in the same conditions, the same configuration, and with the same apparatus.

For a reflective sample, the measurement of $A_p$ may be realized by replacing the sample S by a neutral reflecting material in the optical range of the measurement.

For a transmissive sample, the measurement of $A_p$ may be realized by simply removing the sample S.

Optionally some preprocessing, such as smoothing or averaging may be applied to the measured spectrum.

In an embodiment the spectral range for the measurement is visible ([0.4 μm; 0.8 μm]), and/or near IR (for example included in [0.8; 3 μm]), and/or another bandwidth in the IR.

Then the method comprises a third step 115 of determining a spectral energy $E_{s+p}$ of the measured spectrum $A_{s+p}$ of the sample through the translucent material ($A_{s+p}$).

In signal processing, the spectral energy of a signal is a quantity proportional to the integral of the signal. Here the signal is the measured spectrum As+p function of wavelength $\lambda$. Thus the spectral energy $E_{s+p}$ is proportional to the integration on wavelength of $A_{s+p}$:

Considering a discrete number of wavelengths hi for the measurement of the spectrum, index i varying from 1 to m, then $E_{s+p}$ can be written as:

$$E_{s+p} \propto \sum_{i=1}^{m} A_{s+p}(\lambda_i) \quad (6)$$

Or in a general case:

$$E_{s+p} \propto \int_{\lambda_1}^{\lambda_m} A_{s+p}(\lambda) \cdot d\lambda \quad (7)$$

Then the method comprises a fourth step 120 consisting of estimating a coefficient $\hat{\gamma}$ from the spectral energy $E_{s+p}$ of the measured spectrum $A_{s+p}$ of the sample performed through a translucent material P.

The method further comprises a step 130 of determining the corrected spectrum $\hat{A}_s$ of the sample from the measured spectrum $A_{s+p}$ of the sample and from a corrected spectrum of the translucent material $\hat{A}_p$.

The corrected spectrum of the translucent material $\hat{A}_P$ is determined from the measured spectrum of the translucent material $A_P$ and from the estimated coefficient $\hat{\gamma}$.

Indeed, after a lot of experimentation and reasoning, the inventors have found that a coefficient $\hat{\gamma}$ permitting the correction of the effect of the presence of the translucent material P during the spectrum measurement can be related to the spectral energy of the distorted measurement. The estimated coefficient γ may be obtained by a predetermined relationship R between $E_{s+p}$ and $\hat{\gamma}$:

$$\hat{\gamma} = f(E_{s+p}) \tag{8}$$

It will be explained further in the document how this relation may be determined, leading to an example of such a relationship.

The corrected spectrum $\hat{A}_s$ is a spectrum obtained from the loaded measured spectrum $A_{s+p}$ but being less distorted by the presence of the material P during the measurement. This is possible because the spectrum $A_p$ of the material has been predetermined and loaded. The spectrum Ap may be either measured, or be loaded from a material database. In this last case, the chemical type of the material P has to be known.

The estimated coefficient $\hat{\gamma}$ permits to determine a corrected spectrum of the translucent material $\hat{A}_p$ which is itself used to correct the measured spectrum $A_{s+p}$.

The corrected spectrum $\hat{A}_s$ may be used for classification of the sample, or classification or quantification of a compound present in the sample as explained below. The fact that the spectrum has been corrected will decrease the error rate due the presence of the material P during the measurement of classification/quantification models using the spectrum as input, as described in the background.

Preferably the measured spectra $A_{s+p}$ and $A_P$. are expressed as absorbance defined by formula (1) (or formula (2)), depending on the context and in a consistent way.

In an embodiment of the method as claimed the corrected spectrum of the translucent material $\hat{A}_p$ is determined from the product of the estimated coefficient $\hat{\gamma}$ by the measured spectrum of the translucent material $A_p$:

$$\hat{A}_p = \hat{\gamma} A_p \tag{9}$$

In an embodiment, it is possible to introduce the coefficient $\hat{\gamma}$ in formula (3) such as the corrected spectrum $\hat{A}_s$ of the sample is determined by subtracting the corrected spectrum of the translucent material $\hat{A}_p$ from the measured spectrum $A_{s+p}$ of the sample through the translucent material:

$$\hat{A}_s = A_{s+p} - \hat{\gamma} A_p \tag{10}$$

Formula (10) corresponds to the model described in formula (3) with the adjunction of a coefficient $\hat{\gamma}$ into $A_P$ in order to better take into account the influence of the material P on the measured spectrum. This coefficient according to the invention has a specific relationship R with an intrinsic feature of the measurement itself $A_{s+p}$ via the spectral energy $E_{s+p}$.

Once the estimated spectrum $\hat{A}$ determined by the method 10 is obtained, this spectrum may be used as input into a characterization model.

Figure 6:
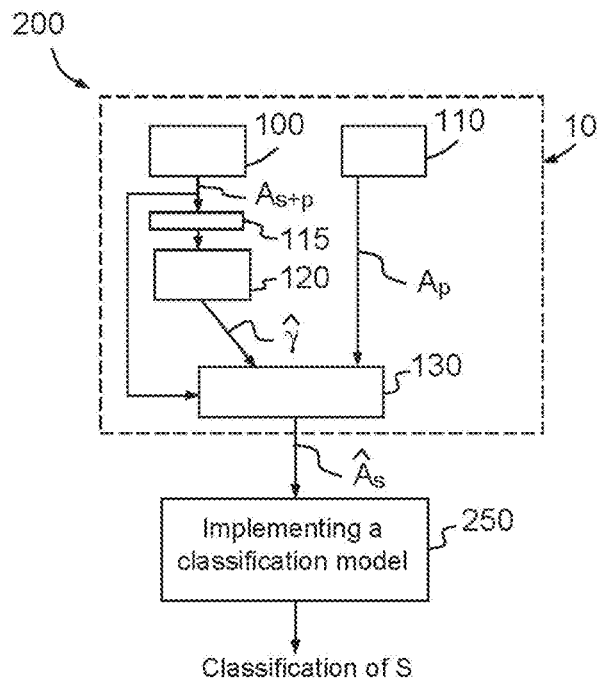
FIG. 6 illustrates a first example of application of the use of the corrected spectrum, which is a classification of the sample, based on the method of FIG. 5.

A first example of application for the use of $\hat{A}$, illustrated on FIG. 6; is a method 200 of classification of a sample S based on the method 10 for determining a corrected spectrum $\hat{A}_s$ of the sample and further comprising a step 250 of implementing a classification model CM developed from a first reference database DB1 as explained above. The classification model CM uses the corrected spectrum $\hat{A}_s$ of the sample as input, and delivers a classification of the sample. Because the initial spectrum $A_{s+p}$ has been corrected by being transformed into $\hat{A}_s$, the error rate of the model CM is decreased. An example is the determination of the flour type among 9 different predetermined types.

Figure 7:
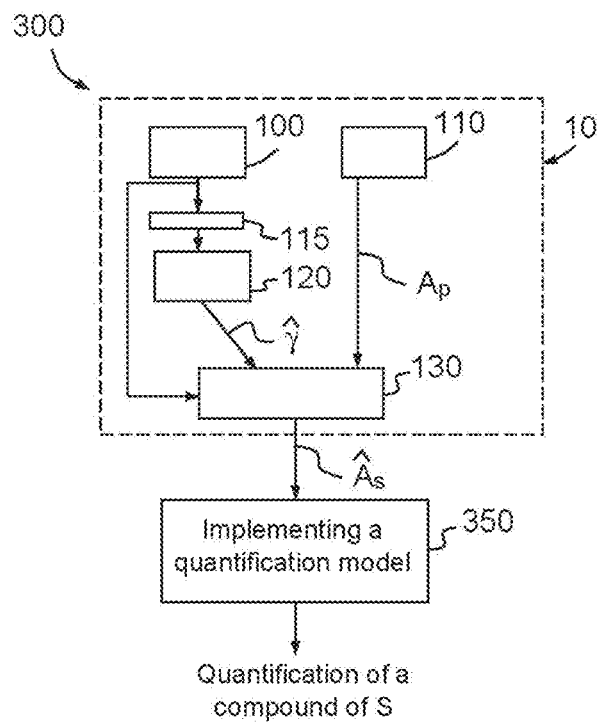
FIG. 7 illustrates a second example of application of the use of the corrected spectrum, which is the quantification of a compound present in the sample, based on the method of FIG. 5.

A second example of application for the use of $\hat{A}$, illustrated on FIG. 7, is a method 300 of quantification of a chemical compound C present in a sample S, based on the method 10 for determining a corrected spectrum $\hat{A}_s$ of the sample and further comprising a step 350 of implementing a quantification model QM developed from a second reference database DB2. The quantification model uses the corrected spectrum $\hat{A}_s$ of the sample as input, and delivers a quantification of the compound C present in the sample. For example it may be the humidity level or the gluten level in the flour.

A mixed application is a classification of a sample using a quantification of a compound, the class of sample being determined as a function of the quantification. For example, two different classes of flour may be defined depending on the percentage of the compound in the flour, above or below a predetermined threshold.

In parallel with elaboration of method 10 by using coefficient $\hat{\gamma}$, the inventors have developed a method for structuring the initial spectra As(λ) of reference samples (or a pre-processed spectrum), which are preferably expressed as an absorbance, by using a method of dimension reduction, as explained in the following paragraphs.

Indeed a spectrum As(λ) has generally a substantial number of abscissa λi, i from 1 to m, m typically being equal to hundreds or thousands, and it may be desired to reduce this number as explained below. For this purpose a method called principal component analysis (PCA) is used.

Figure 8:
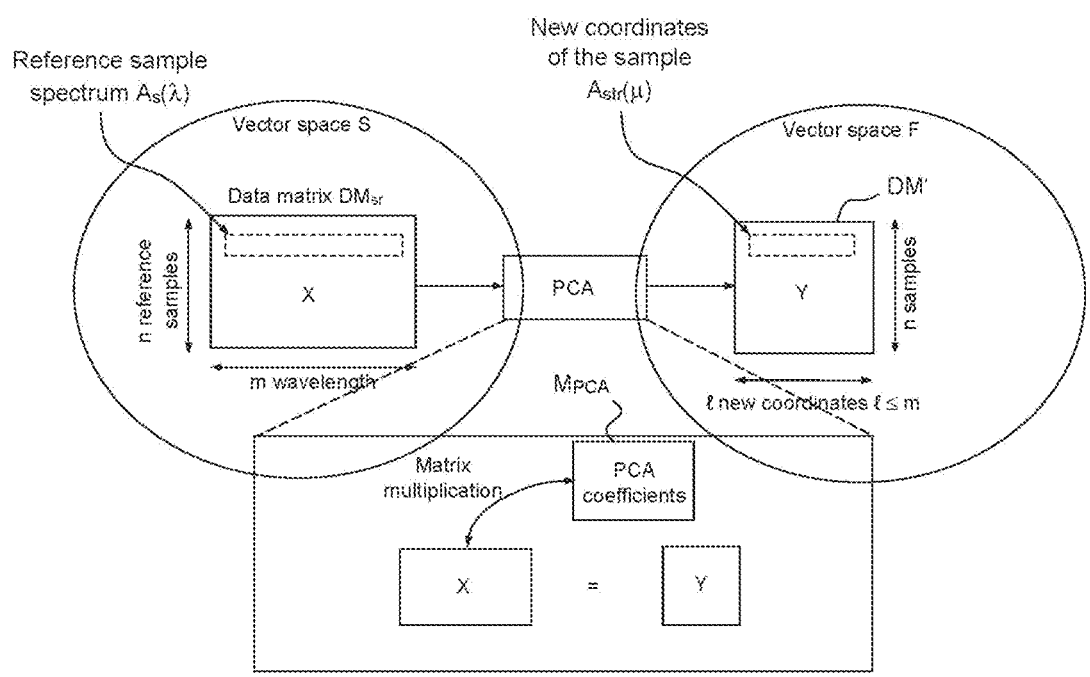
FIG. 8 illustrates the principle of Principal Component Analysis PCA, applied to a spectrum and permitting a change of space on the data matrix.

The principle of the PCA according to the invention, permitting a change of space on the data matrix comprising measured spectra is illustrated on FIG. 8.

Figure 1:
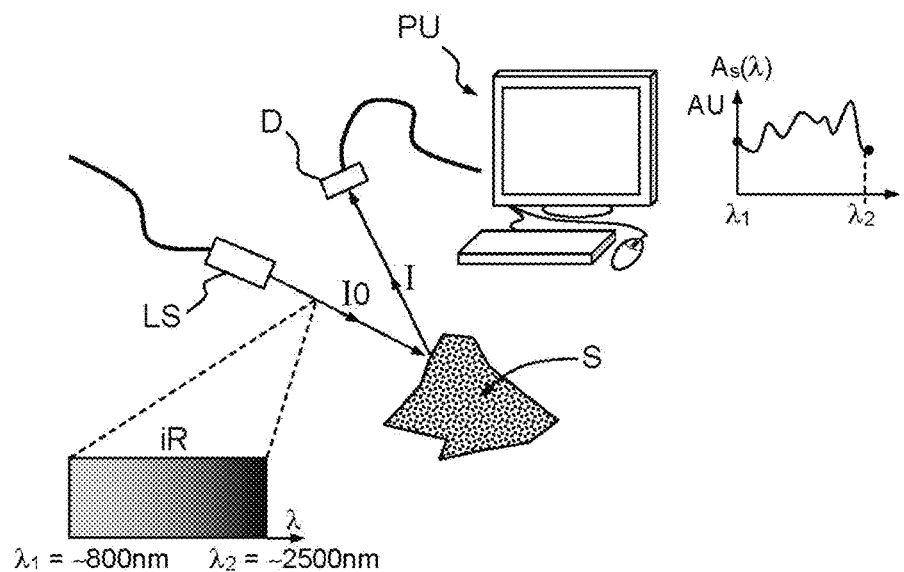
FIG. 1 is a schematic of a spectrometric measurement of a reflective sample.
Figure 2:
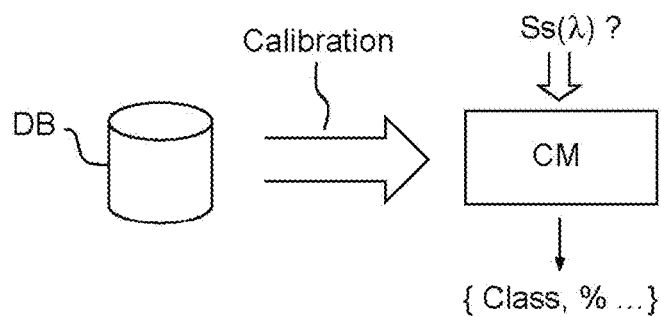
FIG. 2 shows the elaboration and implementation of a characterization model.
Figure 3A:
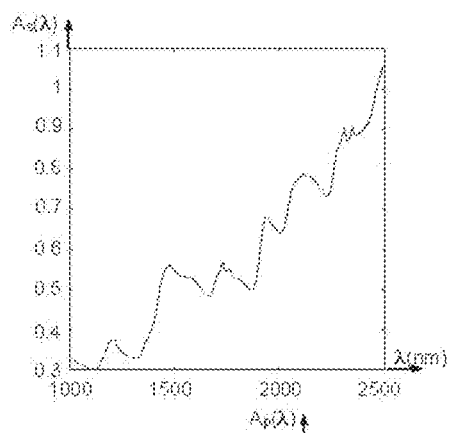
FIGS. 3a-3c show different spectra.
Figure 3B:
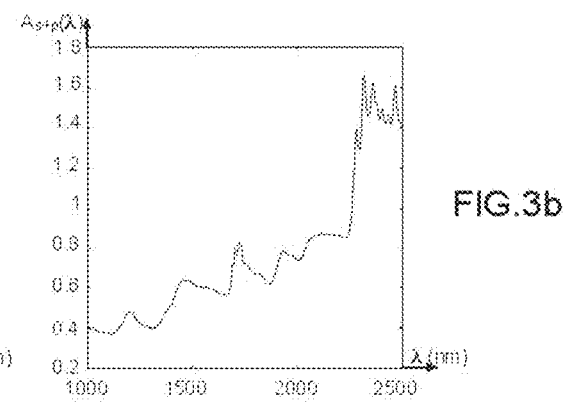
Figure 3C:
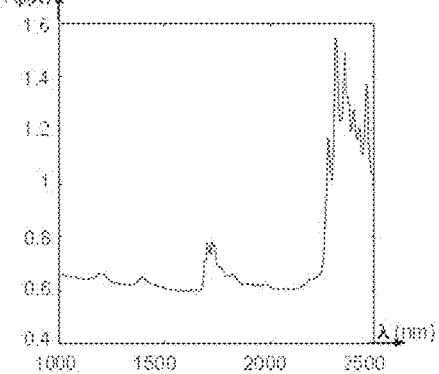

The departure space vector is the spectral space S containing the measured spectrum as a function of wavelength, that is to say the data matrix DMsr of the spectrum of the reference samples (n reference samples) of the reference database DB which is used to elaborate the characterization model (see FIG. 2). The dimension of S is m.

A PCA algorithm is used on a DMsr containing n samples.

The arrival vector space $\mathcal{F}$ is an orthogonal space of dimension I, with I≤m, with new coordinates $\mu_j$, defining a new matrix DM' of n "samples" Astr(μ).

In practice the PCA algorithm determined a coefficient matrix $M_{PCA}$ which is the transfer matrix from δ to $\mathcal{F}$:

$$Y = X \times M_{PCA} \tag{11}$$

The analysis in principal components uses different criteria consisting of maximizing the variance of data and of orthogonalizing the resulting coordinates.

Among $\mu_j$, it is possible to choose only the 2 or 3 first coordinates (μ1, μ2, μ3) which concentrate all the needed information. By construction, coordinates are sorted in a way that the first ones explain the greatest part of the variance in the data. Because spectral data are often highly correlated, the information can be summarized in a few new coordinates. Therefore, it is usual that the three first new coordinates are sufficient to represent the original data.

The matrix of coefficient $M_{PCA}$ is representative of the way the data are organized. In the flour example, the coefficients highlight the differences between the flours. Actually the coefficients may be a weighting factor applied to the values of absorbance of the spectrum of DMs.

PCA analysis may be used as an analysis and visualization technique. Attention is paid to the new coordinates μj named "scores".

In the context of the invention, the determined coefficients $M_{PCA}$ (from the data matrix of reference samples DMsr) are used on another matrix.

A first option is to use them on the measured spectrum $A_{s+p}$ obtained by method 10 as illustrated in FIG. 8bis to generate a structured spectrum $A'_{s+p}(t)$.

Figure 9:
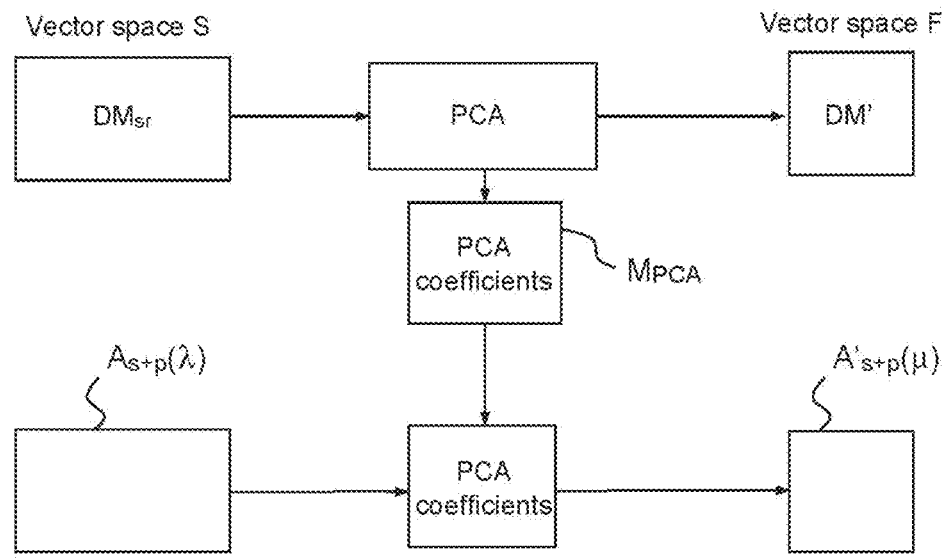
FIG. 9 illustrates the use of a new characterization model developed taking into account the change of variable from $\lambda$ to $\mu$, this model being applied to the spectrum of the sample to characterize.
Figure 9:
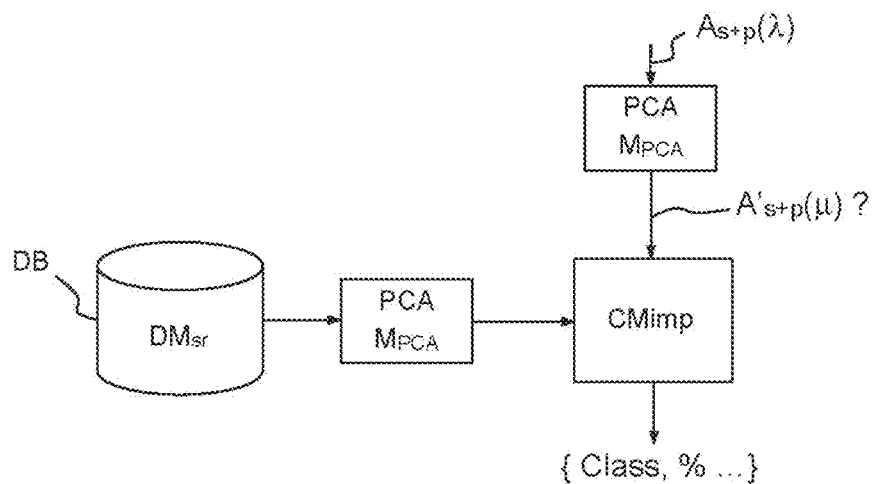

A new characterization model CMimp is developed taking into account the change of variable from λ to μ as illustrated in FIG. 9, and this model CMimp is applied to the spectrum of the sample to be characterized. The initial spectrum $A_{s+p}(\lambda)$ has also to be structured by the PCA coefficient before being used as input for CMimp, and is transformed into $A'_{s+p}(p)$. The number of variable μ is I, with I≤m, and among those I, only the first 2 or 3 variables may be used for calculation: μ1, μ2 μ3.

By applying the PCA coefficients to the spectrum through the translucent material P, this data is transposed into a new space structured in such a way that the classification/quantification operation is greatly simplified, despite the presence of the material P during the measurement. Thus the improved characterization model CMimp delivers a classification of the sample or a classification or a quantification of a compound present in the sample in place of the classification model CM.

By applying the model of flour classification described above, the inventors have found that by using optimized structuration of the spectra by a dimension reduction such as PCA, thus using a transformation based on PCA coefficients $M_{PCA}$, the error rate for spectra of samples performed through the translucent material P became (the corresponding rate without PCA is provided between parenthesis; see also table 1 below).

PE1: 2% (75%)
PE2: 6% (65%)
PET1: 34% (88%)
PET2: 15% (88%)

Thus a result of this first option is that the error rate can be improved by dimension reduction alone.

As a second option corresponding to another embodiment of the invention, such PCA coefficients $M_{PCA}$ (calculated as explained above) are applied to the corrected spectrum $\hat{A}_s$ obtained in method 10.

An aspect of the invention is thus a method 10 comprising a step 140 of structuring the corrected sample spectrum $\hat{A}_s(\lambda)$ based on a principal component analysis PCA, to generate a structured corrected sample spectrum $\hat{A}_{str}(p)$ in order to reduce the plurality of wavelengths λi (I between 1 and m) of the measurement into an lower number of variables μ1, μ2, μ3. The example of FIG. 10 illustrates the particular embodiment of formula (5).

Figure 10:
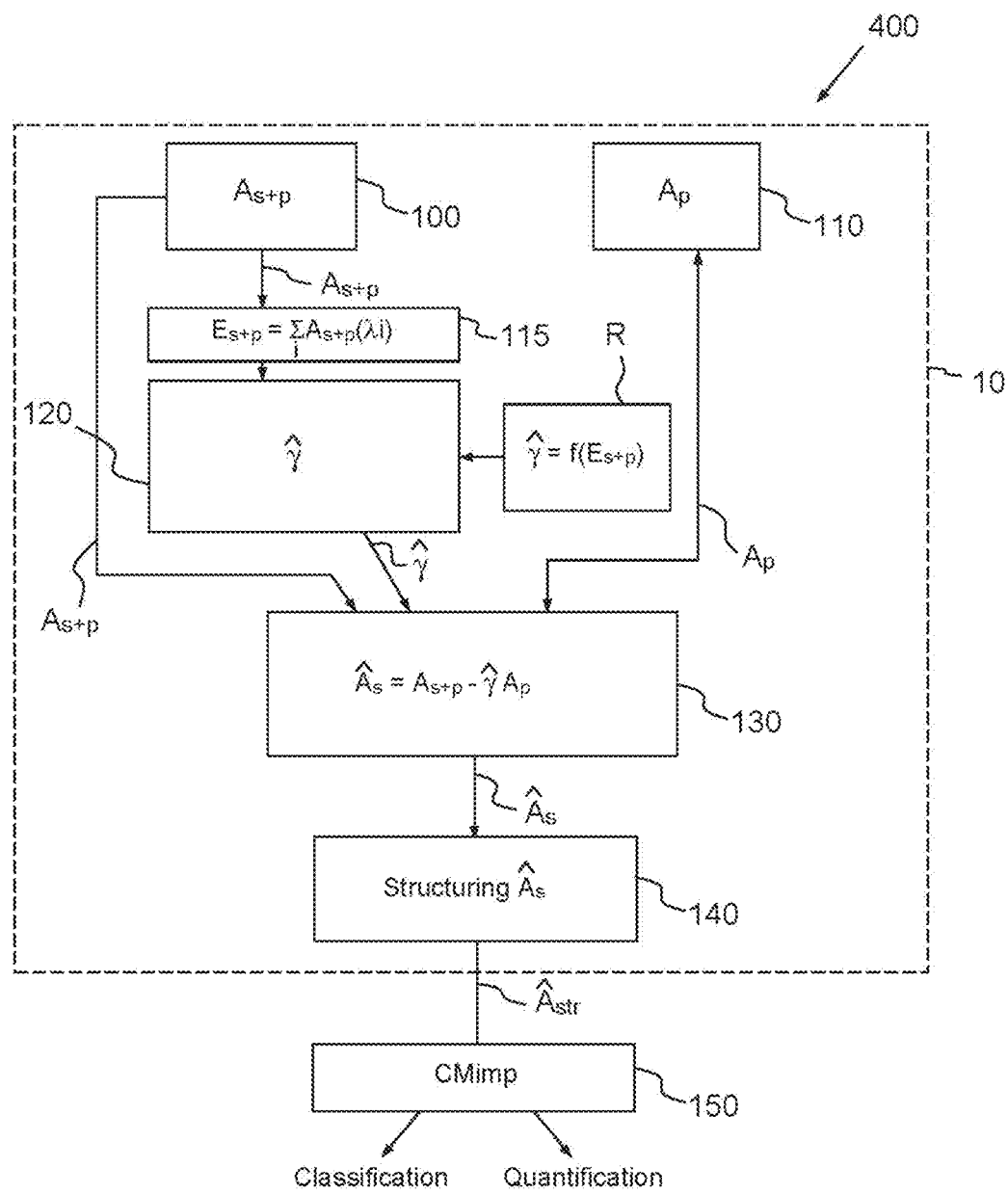
FIG. 10 illustrates a second option corresponding to a preferred embodiment of the invention, where PCA is applied to the corrected spectrum $\hat{A}_s$ obtained by the method of FIG. 5. The characterization method uses an adapted characterization model CMimp.

The additional step 140 of structuring $\hat{A}_s$ may be included in a characterization method 400 using an adapted characterization model CMimp, implemented in a step 150, also illustrated in FIG. 10.

For example, the characterization model may be a classification or a quantification model.

Figure 11:
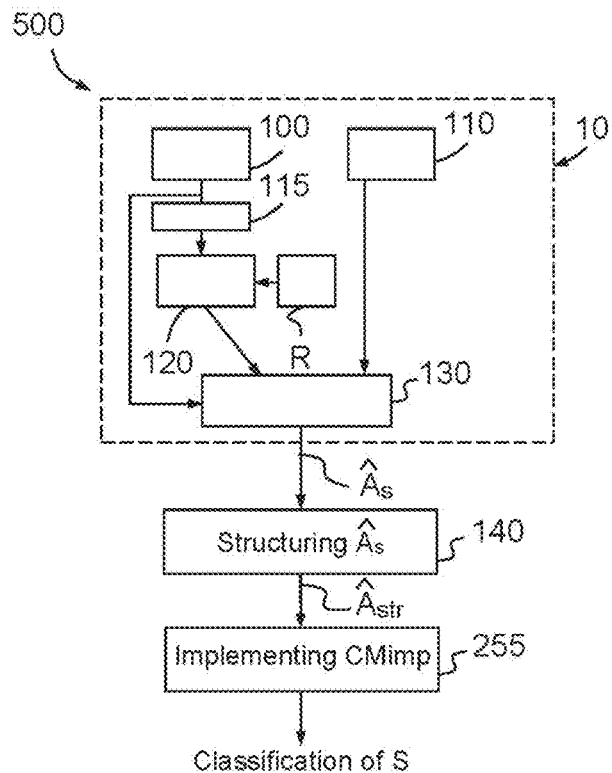
FIG. 11 illustrates a classification method using an adapted classification model.

FIG. 11 illustrates an additional step 140 of structuring $\hat{A}_s$ included in a classification method 500 using an adapted classification model CIMimp, implemented in a step 255.

Figure 12:
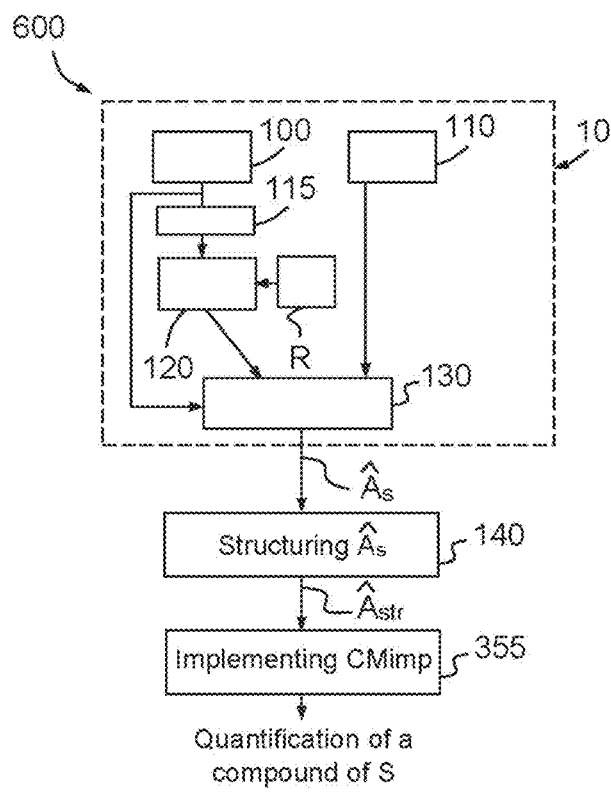
FIG. 12 illustrates a quantification method using an adapted quantification model.

FIG. 12 illustrates an additional step 140 of structuring $\hat{A}_s$ included in a quantification method 600 using an adapted quantification model QMim, implemented in a step 355.

In the flour example, by applying the correction of formula (2) in combination with dimension reduction (PCA), that is to say subtracting the packaging spectrum with $\Upsilon = 1$, the error rate becomes (see also table 1 below):

PE1: 2%
PE2: 5%
PET1: 35%
PET2: 14%

So applying formula (2) ($\Upsilon = 1$) to generate a "pseudo corrected" spectrum in combination with PCA does not improve the error rate compared to PCA alone.

By applying PCA on an improved spectrum $\hat{A}_s$ obtained by using an estimated coefficient $\hat{\gamma}$ however, the error rate is decreased drastically.

In the flour classification example, by applying formula (5) and estimating $\hat{\gamma}$ by the method described above, the following results are obtained (see table 1):

TABLE 1

| Translucent material P | PCA + formula(5) (γ̂) Error rate | PCA + formula(2) ($\Upsilon = 1$) Error rate | PCA alone Error rate | Initial error rate |
|---|---|---|---|---|
| PE1 | 0% | 2% | 2% | 75% |
| PE2 | 4% | 5% | 6% | 65% |
| PET1 | 15% | 35% | 34% | 88% |
| PET2 | 10% | 14% | 15% | 88% |

It can be seen, by comparison with the results obtained with $\Upsilon = 1$ above, that the combination of the correction of the spectrum by using an estimated coefficient $\hat{\gamma}$ ($\hat{\gamma} \neq 1$) with a structuration by PCA of the corrected spectrum leads to a very powerful treatment permitting the recovery of a very low error rate, thus rendering the characterization model robust to the presence of a disturbing material P during the measurement.

Figure 13:
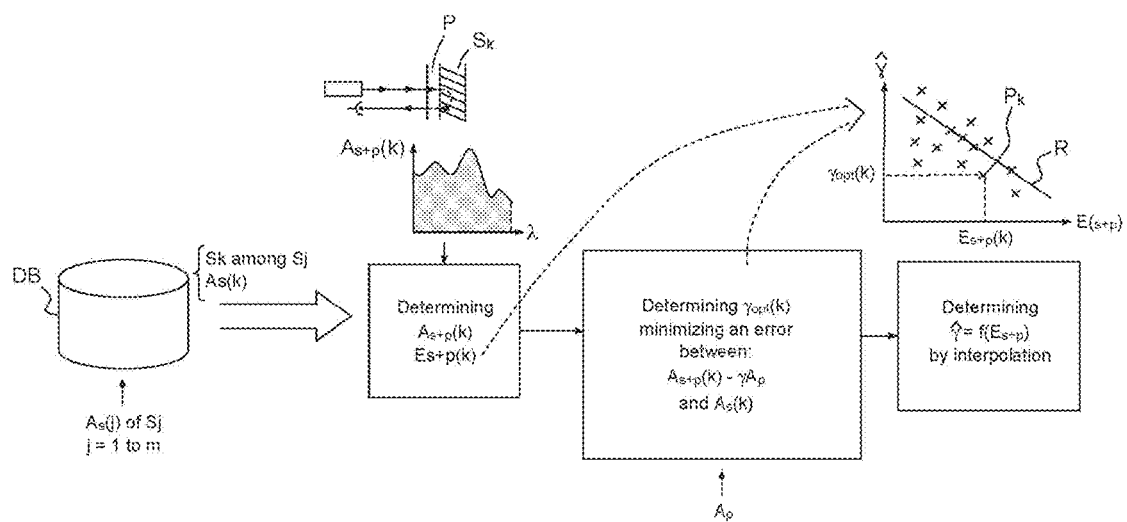
FIG. 13 shows an example of the way to determine the relationship between the spectral energy of the measured spectrum and the estimated coefficient.

Now a way to determine the relationship R between the spectral energy $E_{s+p}$ of the measured spectrum $A_{s+p}$ and the estimated coefficient $\hat{\gamma}$ is described and illustrated on FIG. 13.

$$R: \hat{\gamma} = f(E_{s+p})$$

The starting point is the realization of the database BD of reference sample used to develop the characterization model. This data base contains measured spectrum As(j) of reference samples Sj, with j=1 to m.

In a first step k samples Sk among the j samples Sj are chosen, k<j, on specific criteria. For those chosen reference samples Sk in a measured spectrum $A_{s+p}(k)$ through the translucent material P of a known chemical nature is performed.

In a second step for each k the corresponding spectral energy $E_{s+p}(k)$ is determined by integration.

In a third step for each k [$A_{s+p}(k)$, $E_{s+p}(k)$] an optimized coefficient $\Upsilon_{opt}(k)$ is determined minimizing an error between $A_{s+p}(k) - \Upsilon Ap$ on one side and As(k) on the other side. This calculation can be performed because for those samples Sk both $A_{s+p}$ and $A_s$ are known.

Preferably $\gamma_{opt}(k)$ minimizes RMSE(k):

$$\gamma_{opt}(k) = \underset{\gamma \in [0;2]}{\mathrm{argmin}}\{RMSE(k, \gamma)\} \quad (12)$$

With:

$$RMSE(k, \gamma) = \sqrt{\frac{1}{m}\sum_{i=1}^{m}\{[A_{s+p}(k) - \gamma A_p](\lambda_i) - A_s(k)(\lambda_i)\}^2} \quad (13)$$

In a fourth step the cloud of points Pk with Pk having the coordinates: $\{E_{s+p}(k), \gamma_{opt}(k)\}$ is considered. This cloud of points provides a picture of the link between the optimized coefficient and the spectral energy for a certain number of samples. To obtain a general law, the relationship R: $\hat{\gamma}=f(E_{s+p})$ is determined by interpolation. This relationship constitutes the predetermined relationship which is used in step 120 of method 10.

This method permits the establishment of a law based on practical measurement and representative of the effect of the material P corrupting the measurement, and thus the correction of such effect via the estimated coefficient $\hat{\gamma}$.

Figure 14A:
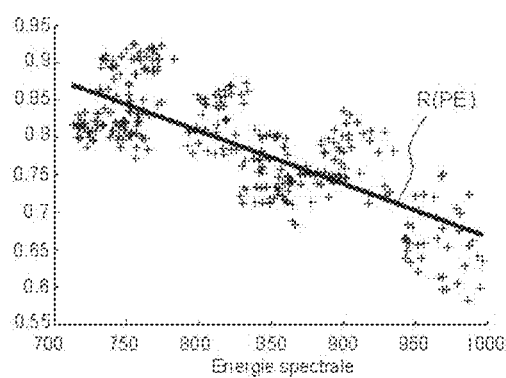
FIGS. 14a and 14b illustrate illustrates the cloud points obtained in a flour classification example, FIG. 14a for PE as the translucent material P and FIG. 14b for PET as material P.
Figure 14B:
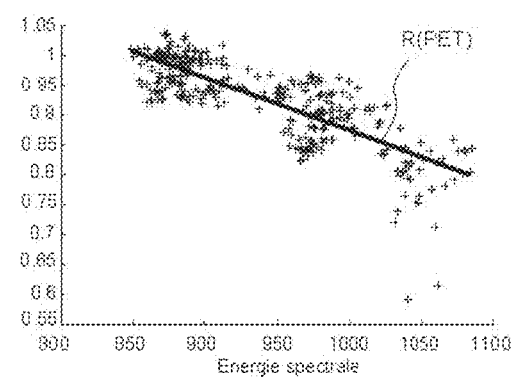

FIG. 14 illustrates the cloud points obtained in the flour example, FIG. 14a for PE as the translucent material and FIG. 14b for PET as P material.

In order to obtain the regression model, thirty measurements have been taken for each type of flour (eight different types of flours, those considered for the classification model) with a given packaging. Each point on the FIGS. 14a and 14b corresponds to the $\{E, \gamma\}$ coordinates of each measurement of each flour (leading to 240 points for each regression plot).

In the case illustrated on FIGS. 14a and 14b, the function R determined by interpolation is linear:

$$\hat{\gamma} = aE_{s+p} + b \quad (14)$$

Figure 15:
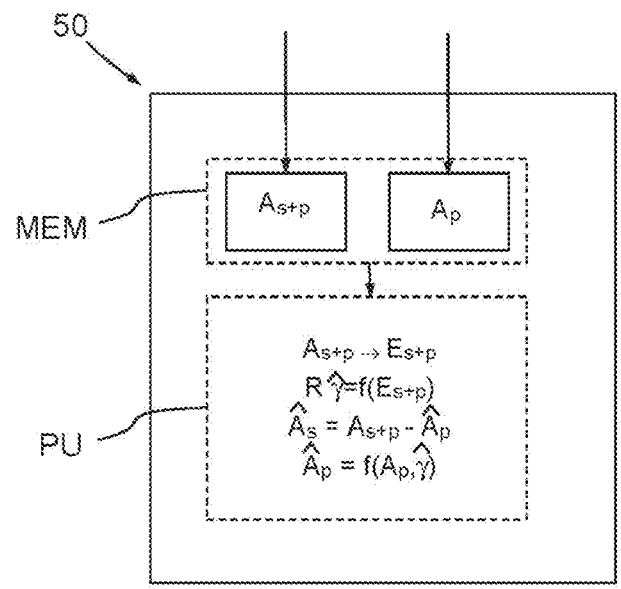
FIG. 15 shows a characterization device for characterizing a sample according to another aspect of the invention.

According to another aspect the invention concerns a characterization device 50 for characterizing a sample S illustrated on FIG. 15.

The device comprises a memory MEM storing a measured spectrum $A_{s+p}$ of the sample S, performed through a translucent material P, and a measured spectrum of the translucent material $A_p$. This spectrum Ap may be obtained by a measurement made the same way as the sample spectrum or may be available from a database DBP insofar as its chemical type is known.

The device 50 further comprises a processing unit PU configured to:
estimate a coefficient $\hat{\gamma}$ from a spectral energy $E_{s+p}$ of the measured spectrum $A_{s+p}$ of the sample through the translucent material P and,
determine a corrected spectrum ($\hat{A}_s$ of the sample from the measured spectrum $A_{s+p}$ of the sample through the translucent material and from a corrected spectrum of the translucent material $\hat{A}_p$.

The corrected spectrum of the translucent material $\hat{A}_P$ is determined from the measured spectrum of the translucent material $A_P$ and from the estimated coefficient $\hat{\gamma}$.

The corrected spectrum of the sample $\hat{A}_s$ is intended to be used for classification of the sample, or classification or quantification of a compound present in the sample.

Figure 16:
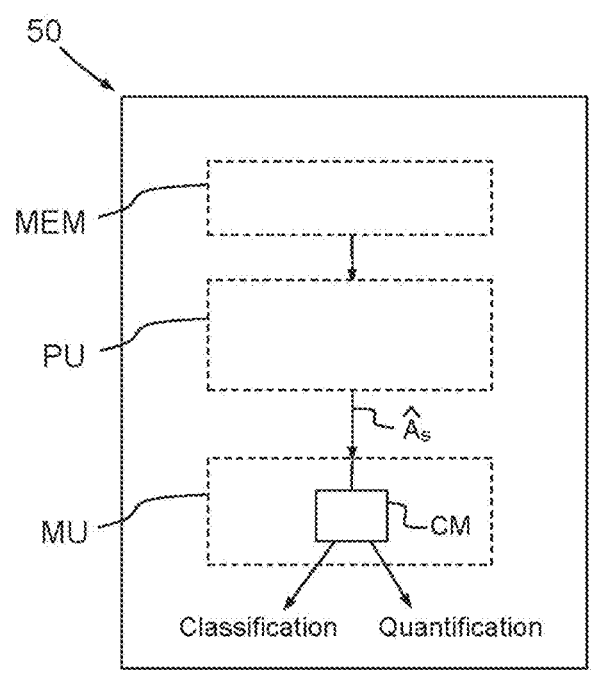
FIG. 16 illustrates a particular embodiment of the characterization device according to the invention.

In a particular embodiment illustrated on FIG. 16 the characterization device 50 further comprises a modelling unit MU configured to implement a characterization model CM developed from a reference database DB, using the corrected spectrum $\hat{A}_s$ of the sample as input. The modelling unit delivers a classification of the sample or a classification or a quantification of a compound present in the sample.

Figure 17:
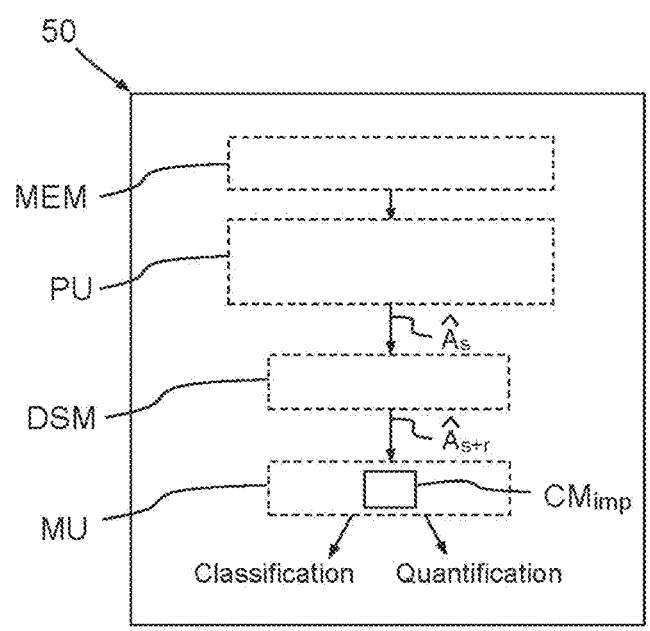
FIG. 17 illustrates a preferred embodiment of the characterization device according to the invention.

The characterization device 50 further comprises a data structuring module DSM, as illustrated in FIG. 17, the DSM being configured for structuring the corrected sample spectrum $\hat{A}_s$ based on a principal component analysis such as PCA, in order to generate a structured corrected sample spectrum $\hat{A}_{str}$. This structuring reduces the plurality of wavelengths hi of the measurement into an lower number of variables such as µ1, µ2 µ3.

The structured corrected sample spectrum $\hat{A}_{str}$ is the input of a improved characterization model CMimp developed from a reference database DB and taking into account the structuration of $\hat{A}_{str}$.

Figure 18A:
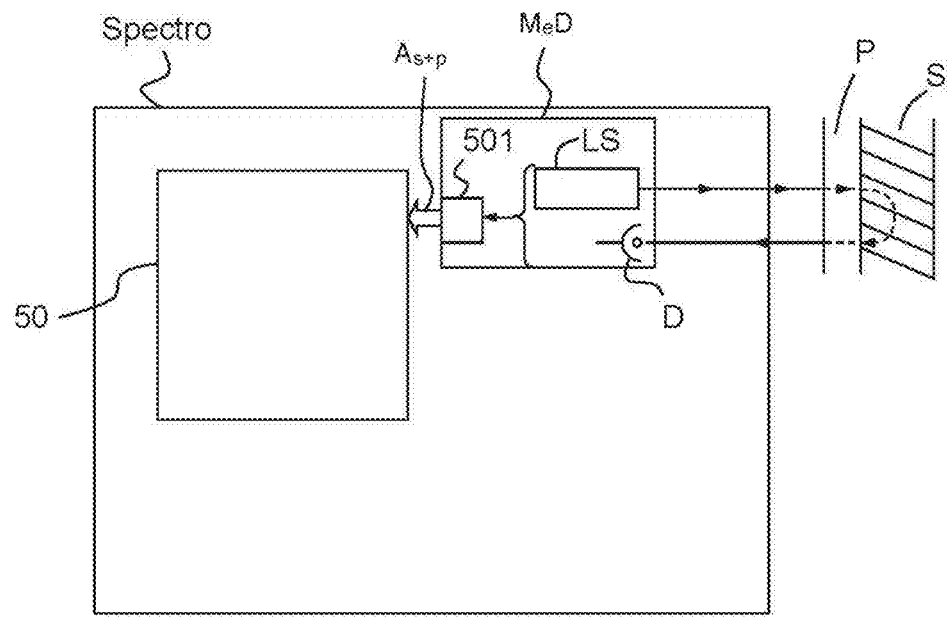
FIG. 18a shows a spectrophotometer according to another aspect of the invention.

According to another aspect, the invention concerns a spectrophotometer Spectro as illustrated in FIG. 18a and comprising:
a measuring device MeD comprising:
a light source LS configured to illuminate the sample S to characterize, the sample being illuminated through a translucent material P. The light source may be a laser or a lamp.
a detector D configured to detect the light reflected from or transmitted by the sample,
a calculation module 501 configured to generate a measured spectrum $A_{s+p}$ of said sample, from the measured incident light source illuminating the sample and the reflected/transmitted light by the sample. The calculation module may include preprocessing.
a characterization device 50 as illustrated in FIGS. 15 to 17.

The spectrometer Spectro according to the invention is thus capable of measuring the spectrum of the sample S through a material P which may degrade the measurement, and performing an accurate characterization of the sample despite the presence of the material P during the measurement.

In one embodiment, the spectrum of the translucent material $A_p$ is measured the same way as the sample, with the light source LS, the detector D and the calculation module. In this case it is not necessary to know the chemical type of the translucent material.

Figure 18B:
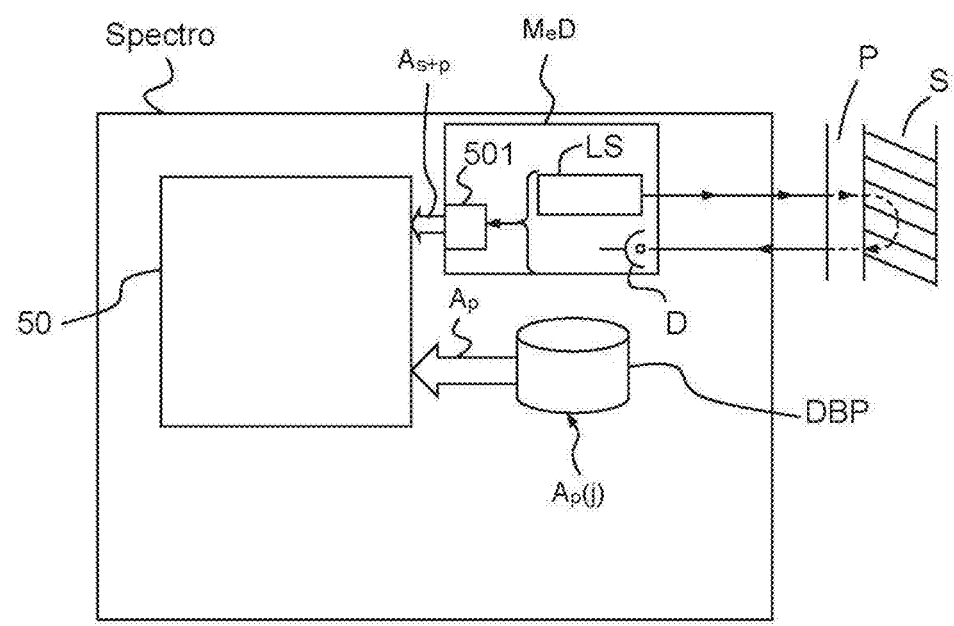
FIG. 18b shows another spectrometer according to the invention.

In another embodiment, the chemical type of the translucent material P is identified, and the spectrum Ap is loaded from a material database DBP, which can be either included in Spectro, as shown in FIG. 18b, or located in a different element.

It will be appreciated that the foregoing embodiments are merely non limiting examples. In particular, the measuring device MeD, the characterization device 50 and the material database DBP may be located in different elements and used together in any combination.

Figure 19:
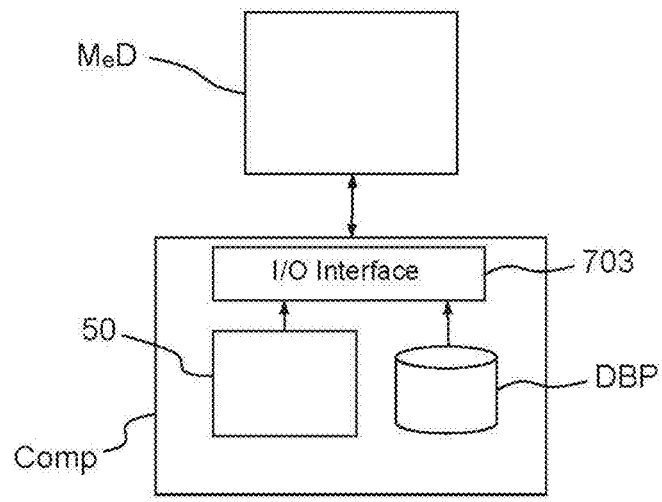
FIG. 19 illustrates an embodiment of the invention where the measuring device, the characterization device and the material database may be located in different elements.

In an embodiment MeD may be linked to a computer Comp via an I/O interface 900, the characterization device 50 and the material database DBP being located in the computer, as illustrated in FIG. 19; part of the calculation module 501 may also be located in the characterization device.

Figure 20:
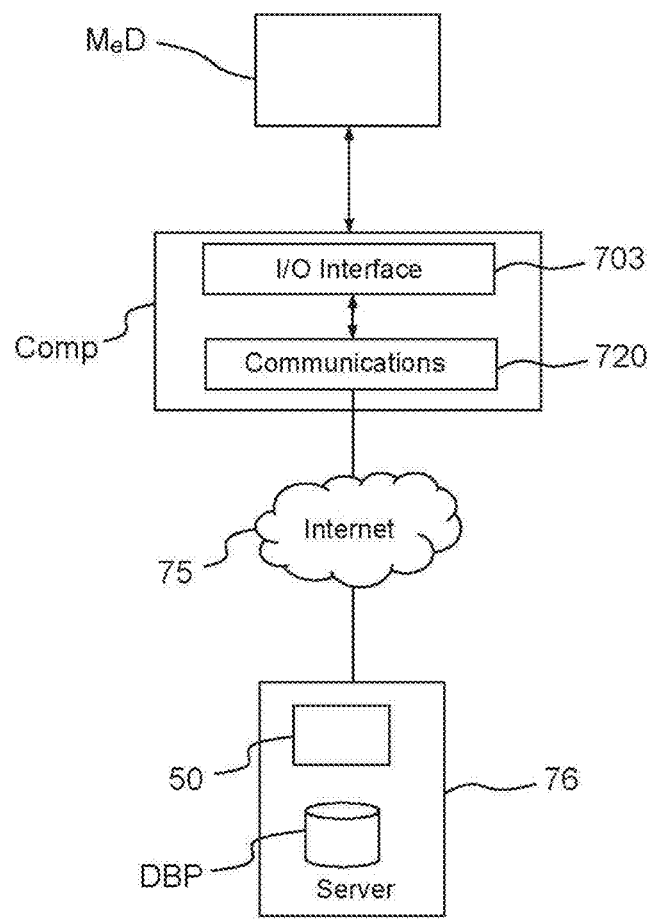
FIG. 20 illustrates another embodiment of the invention where the characterization device and/or material database may be located in a remote server linked via internet to the communication subsystem of a computer.

In another embodiment characterization device 50 and/or material database DBP may be located in a remote server 76 linked via internet 75 to the communication subsystem 720 of a computer Comp, as illustrated in FIG. 20.

The disclosed methods 10, 200, 300, 400, 500, 600, can take form of an entirely hardware embodiment (e.g. FPGA), an entirely software embodiment (for example to control a device according to the invention) or an embodiment containing both hardware and software elements. Software embodiments include but are not limited to firmware, resident software, microcode, etc. The invention can take the form of a computer program product accessible from a computer-usable or computer-readable medium providing program code for use by or in connection with a computer or an instruction execution system.

A computer-usable or computer-readable embodiment can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium.

In some embodiments, the methods described herein may be implemented in whole or part by a user device. These methods and processes may be implemented by computer-application programs or services, an application-programming interface (API), a library, and/or other computer-program product, or any combination of such entities.

The user device may be a mobile device such as a smart phone or tablet, a computer or any other device with processing capability, such as a robot or other connected device.

Figure 21:
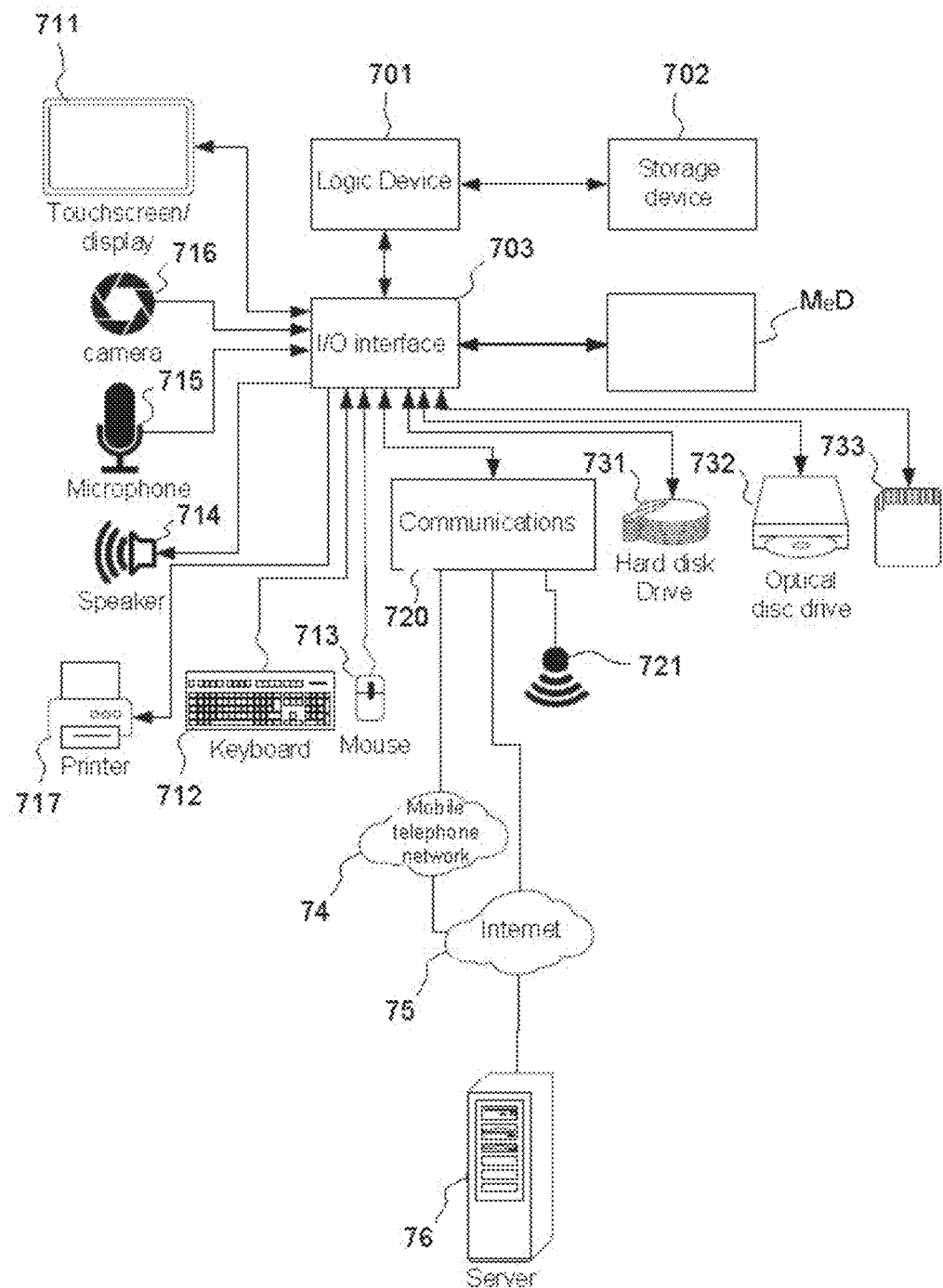
FIG. 21 shows a generic computing system suitable for implementation of embodiments of the invention.

FIG. 21 shows a generic computing system suitable for implementation of embodiments of the invention. A shown in FIG. 21, a system includes a logic device 701 and a storage device 702. The system may optionally include a display subsystem 711, input subsystem 712, 713, 714, communication subsystem 720, and/or other components not shown.

Logic device 701 includes one or more physical devices configured to execute instructions. For example, the logic device 701 may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic device 701 may include one or more processors configured to execute software instructions. Additionally or alternatively, the logic device may include one or more hardware or firmware logic devices configured to execute hardware or firmware instructions. Processors of the logic device may be single-core or multi-core, and the instructions executed thereon may be configured for sequential, parallel, and/or distributed processing. Individual components of the logic device 701 optionally may be distributed among two or more separate devices, which may be remotely located and/or configured for coordinated processing. Aspects of the logic device 701 may be virtualized and executed by remotely accessible, networked computing devices configured in a cloud-computing configuration.

Storage device 702 includes one or more physical devices configured to hold instructions executable by the logic device to implement the methods and processes described herein. When such methods are implemented, the state of storage 702 device may be transformed—e.g., to hold different data.

Storage device 702 may include removable and/or built-in devices. Storage device 702 may comprise one or more types of storage device including optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage device may include volatile, nonvolatile, dynamic, static, read/write, read-only, random-access, sequential-access, location-addressable, file-addressable, and/or content-addressable devices.

In certain arrangements, the system may comprise an I/O interface 703 adapted to support communications between the Logic device 701 and further system components. For example, additional system components may comprise removable and/or built-in extended storage devices. Extended storage devices may comprise one or more types of storage devices including optical memory 732 (e.g., CD, DVD, HD-DVD, Blu-Ray Disc, etc.), semiconductor memory 733 (e.g., RAM, EPROM, EEPROM, FLASH etc.), and/or magnetic memory 731 (e.g., hard-disk drive, floppy-disk drive, tape drive, MRAM, etc.), among others. Such extended storage device may include volatile, nonvolatile, dynamic, static, read/write, read-only, random-access, sequential-access, location-addressable, file-addressable, and/or content-addressable devices.

It will be appreciated that storage device includes one or more physical devices, and excludes propagating signals per se. However, aspects of the instructions described herein alternatively may be propagated by a communication medium (e.g., an electromagnetic signal, an optical signal, etc.), as opposed to being stored on a storage device.

Aspects of logic device 701 and storage device 702 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The term "program" may be used to describe an aspect of computing system implemented to perform a particular function. In some cases, a program may be instantiated via logic device executing machine-readable instructions held by storage device. It will be understood that different modules may be instantiated from the same application, service, code block, object, library, routine, API, function, etc. Likewise, the same program may be instantiated by different applications, services, code blocks, objects, routines, APIs, functions, etc. The term "program" may encompass individual or groups of executable files, data files, libraries, drivers, scripts, database records, etc.

In particular, the system of FIG. 21 may be used to implement embodiments of the invention.

For example a program implementing the steps described with respect to FIG. 5, 6, 7, 10, 11, or 12 may be stored in storage device 702 and executed by logic device 701. The material database DBP, the predetermined relationship R and the PCA coefficients needed for structuring may be stored in storage device 702 or the extended storage devices 732, 733 or 731. The Logic device may cause the camera 716 or Near Field interface 721 to send an order to the measurement device MeD to proceed with a measurement $A_{s+p}$ of a spectrum to characterize.

Accordingly the invention may be embodied in the form of a computer program.

Figure 22:
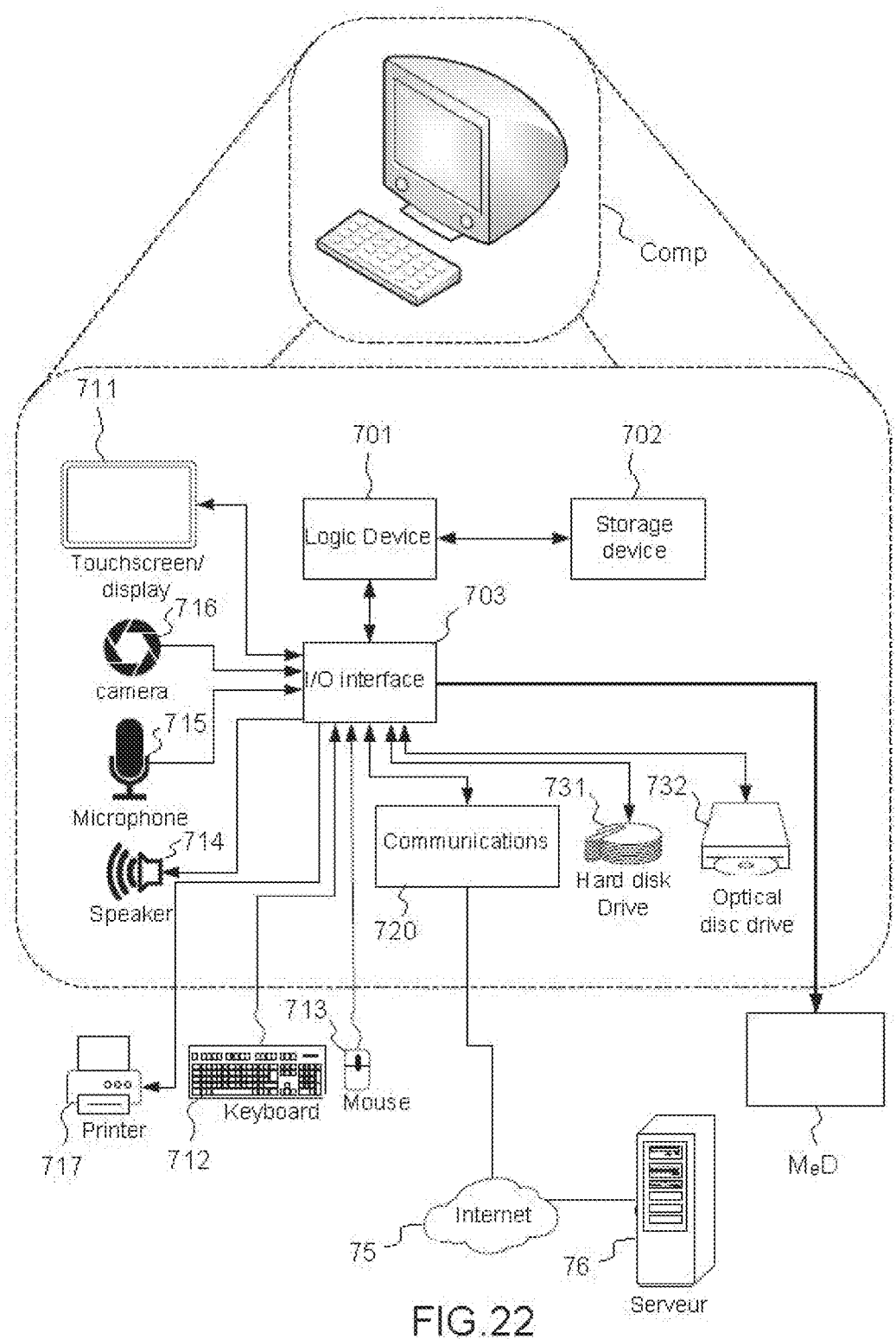
FIG. 22 shows a computer device adaptable to constitute an embodiment of the invention.

FIG. 22 shows a computer device Comp adaptable to constitute an embodiment. As shown in FIG. 21, the computer device incorporates elements 701, 702, 703, 720, 730, 732, 714, 715, 716 as described above. It is in communication with elements 717, 712 and 713 as peripheral devices which may also be incorporated in the same computer device, and with a server 76 via the network 75. On the other hand, elements 733, 721 and 74 are omitted, and element 711 is an ordinary display with or without touchscreen functionality.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

On another aspect, the invention relates to a computer program adapted to implement the steps of the method as claimed. On another aspect the invention relates to a computer readable medium incorporating the computer program.

The invention claimed is:

1. Characterization device for characterizing a sample said device comprising:
    a memory storing a measured spectrum of said sample, performed through a translucent material, and a measured spectrum of the translucent material,
    a processing unit configured to:
        determine a spectral energy of the measured spectrum of the sample through the translucent material, the spectral energy being proportional to an integration on wavelength of the measured spectrum,
        estimate a coefficient from said spectral energy and,
        determine a corrected spectrum of the sample from the measured spectrum of the sample through the translucent material and from a corrected spectrum of the translucent material,
        said corrected spectrum of the translucent material being determined from the measured spectrum of the translucent material and from the estimated coefficient.

2. Characterization device as claimed in claim 1 further comprising a modelling unit configured to implement a characterization model developed from a reference database of spectra of reference samples, said characterisation model using the corrected spectrum of the sample as input, and delivering a classification of the sample or a classification or a quantification of a compound present in the sample.

3. Characterization device as claimed in claim 2, further comprising a data structuring module configured for structuring the corrected sample spectrum based on a principal component analysis, said data structuring module generating a structured corrected sample spectrum, thereby reducing the number of wavelengths of the measurement into a lower number of variables, said structured corrected sample spectrum being the input of an improved characterization model developed from the reference database, said improved characterization model delivering a classification of the sample or a classification or a quantification of a compound present in the sample in place of said classification model.

4. A spectrophotometer comprising:
    a measuring device comprising:
        a light source configured to illuminate a sample, said sample being illuminated through a translucent material,
        a detector configured to detect the light reflected from or transmitted by the sample,
        a calculation module configured to generate a measured spectrum of said sample, and
    a characterization device as claimed in claim 1.

5. Method for determining a corrected spectrum of a sample, comprising:
    storing a measured spectrum of the sample performed through a translucent material,
    storing a measured spectrum of the translucent material,
    determining a spectral energy of the measured spectrum of the sample through the translucent material, the spectral energy being proportional to an integration on wavelength of the measured spectrum,
    estimating a coefficient from said spectral energy,
    determining said corrected spectrum of the sample from the measured spectrum of the sample and from a corrected spectrum of the translucent material,
    said corrected spectrum of the translucent material being determined from the measured spectrum of the translucent material and from the estimated coefficient.

6. Method as claimed in claim 5 wherein said measured spectra are expressed as absorbance.

7. Method as claimed in claim 5 wherein the corrected spectrum of the translucent material is determined from a product of the estimated coefficient and the measured spectrum of the translucent material.

8. Method as claimed in claim 5 wherein the corrected spectrum of the sample is determined by subtracting the corrected spectrum of the translucent material from the measured spectrum of the sample through the translucent material.

9. Method as claimed in claim 5 wherein the estimated coefficient is determined by a predetermined relationship between the spectral energy of the measured spectrum of the sample through the translucent material and the estimated coefficient.

10. Method as claimed in claim 9 wherein the predetermined relationship is a linear function.

11. Method as claimed in claim 5 comprising a previous step of measuring the measured spectrum of the sample through the translucent material.

12. Method as claimed in claim 5, further comprising implementing a characterization model corresponding to a classification model or a quantification model, and using the corrected spectrum of the sample as input.

13. Method as claimed in claim 5 further comprising structuring the corrected sample spectrum based on a principal component analysis to generate a structured corrected sample spectrum, thereby reducing the number of wavelengths of the measurement into a lower number of variables.

14. Method of characterization of a sample comprising a method for determining a corrected spectrum of said sample as claimed in claim 13 and further comprising implementing a characterization model using the structured corrected sample spectrum as input.

15. A non-transitory computer-readable storage medium for determining a corrected spectrum of a sample, comprising computer-executable instructions for:
    storing a measured spectrum of the sample performed through a translucent material,
    storing a measured spectrum of the translucent material,
    determining a spectral energy of the measured spectrum of the sample through the translucent material, the spectral energy being proportional to an integration on wavelength of the measured spectrum, estimating a coefficient from said spectral energy,
determining said corrected spectrum of the sample from the measured spectrum of the sample and from a corrected spectrum of the translucent material,
said corrected spectrum of the translucent material being determined from the measured spectrum of the translucent material and from the estimated coefficient.

* * * * *